United States Patent
Kamiya et al.

(10) Patent No.: US 6,201,121 B1
(45) Date of Patent: Mar. 13, 2001

(54) PROCESS FOR THE PREPARATION OF 3-DIHALOBENZYL-2,4-QUINAZOLINEDIONE DERIVATIVES

(75) Inventors: Takashi Kamiya, Suita; Hiroyuki Takehara, Kamiichi-machi; Yoshitaka Inamoto, Kamiichi-machi; Akihito Taniguchi, Kamiichi-machi; Masayuki Masumoto, Kamiichi-machi, all of (JP)

(73) Assignees: Fuji Chemical Industry Co., Ltd., Nakaniikawa-gun; Fujisawa Pharmaceutical Co., Ltd., Osaka, both of (JP)

( * ) Notice: Subject to any disclaimer, the term of this patent is extended or adjusted under 35 U.S.C. 154(b) by 0 days.

(21) Appl. No.: 09/091,826

(22) PCT Filed: Dec. 27, 1996

(86) PCT No.: PCT/JP96/03878

§ 371 Date: Aug. 18, 1998

§ 102(e) Date: Aug. 18, 1998

(87) PCT Pub. No.: WO97/24335

PCT Pub. Date: Jul. 10, 1997

(30) Foreign Application Priority Data

Dec. 28, 1995 (JP) .................................... 7-343747
Dec. 28, 1995 (JP) .................................... 7-343748

(51) Int. Cl.$^7$ .................................................. C07D 239/72
(52) U.S. Cl. ........................................................... 544/285
(58) Field of Search .......................................... 544/285

(56) References Cited

U.S. PATENT DOCUMENTS 4,883,800 * 11/1989 Hashimoto et al. ................. 544/285

FOREIGN PATENT DOCUMENTS 62-96476   5/1987 (JP) .
3-232885  10/1991 (JP) .

OTHER PUBLICATIONS

Kagara et al JP 01025767, Jan. 27, 1989 Caplus Abstrast p. 9–15, 1989.*
Haslam, E. in Protecting groups in Organic chemistry edited by McOmie, chapter 5, p. 185–215, 1973.*
Chemical Abstracts, 56027, vol. 108, No. 7, Feb. 15, 1988.

* cited by examiner

Primary Examiner—Richard L. Raymond
Assistant Examiner—Venkataraman Balasubramanian
(74) Attorney, Agent, or Firm—Oblon, Spivak, McClelland, Maier & Neustadt, P.C.

(57) ABSTRACT

A process for preparing a 3-dihalobenzyl-2,4-quinazolinedione derivative represented by the formula (V):

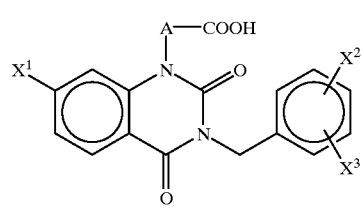

(V)

(wherein
$X^1$, $X^2$, $X^3$ are independently a halogen atom, and
A is an alkylene group),
which comprises:
reacting a dihalobenzyl derivative represented by the formula (III):

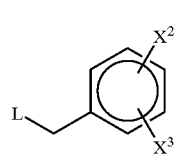

(III)

(wherein
$X^2$ and $X^3$ are each as defined above, and
L is an acid residue)
with a 2,4-quinazolinedione derivative having a carboxyalkyl group represented by the formula (I):

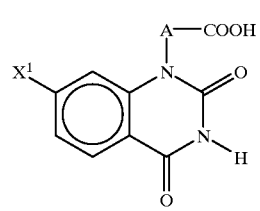

(I)

(wherein $X^1$ and A are each as defined above)
to selectively substitute a hydrogen atom of an imino group at the 3-position of the derivative (1).

The above process enables the efficient preparation of the compounds of the above formula (V) useful as inhibitors against aldose reductases, makes it possible to secure the safety and hygiene of workers, and can facilitate waste disposal to reduce the expenses, thus being industrially extremely advantageous.

9 Claims, No Drawings

PROCESS FOR THE PREPARATION OF 3-DIHALOBENZYL-2,4-QUINAZOLINEDIONE DERIVATIVES

TECHNICAL FIELD

The present invention relates to a process for efficiently preparing a 3-dihalobenzyl-2,4-quinazolinedione derivative represented by FK366 {chemical name: 1-carboxymethyl-3-[(2-fluoro-4-bromo)benzyl]-7-chloro-2,4(1H, 3H)-quinazolinedione}, which is useful as inhibitors against aldose reductases.

More particularly, the present invention relates to a process for preparing a 3-dihalobenzyl-2,4-quinazolinedione derivative, which can be conducted in one pot using a 2,4-quinazolinedione derivative having a carboxyalkyl group at the 1-position of 2,4-quinazolinedione skeleton as the starting material. The process is superior in handling, makes it possible to give the desired compound in a high yield and purity, being useful from the viewpoint of efficiency and the safety and hygiene of workers.

BACKGROUND ART

To prevent and/or treat disorders accompanied with a disorder of polyol metabolism (e.g. neuropathy, retinopathy, nephropathy, etc.) among disorders accompanied with diabetes, the development of representative inhibitors against aldose reductases FK366 represented by the following formula:

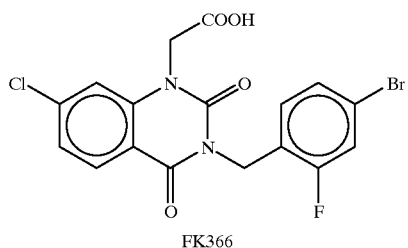

FK366 has been progressed.

To prepare the above FK366, 2,4-quinazolinedione derivative having a carboxyalkyl group represented by the formula (I):

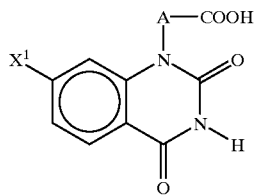

(I)

is an important intermediate. As the process of preparing this intermediate, for example, the following processes have been reported [Chemistry Express, vol.8, no.9, p.761–764 (1993)]:

①: a process of heating N-alkylanthranilic acid with urea and closing the ring,

②: a process of subjecting anthranylamide to introduction reaction of carbonyl group by means of phosgene, and the like, to give a quinazolinedione derivative having carboxyalkyl groups not only at the 1-position but also the 3-position, ③: a process of subjecting a phenylurea derivative obtained by reaction between anthranilic acid and isocyanate to ring-closing reaction to give a quinazolinedione derivative having a carboxyalkyl group at the 3-position, not at the 1-position, ④: a process of comprising: subjecting a quinazolinedione derivative obtained from 4-chloroanthranyl acid to silylation reaction to give a silylquinazoline derivative; selectively reacting the resulting silylquinazoline derivative at the 1-position with ethyl bromoacetate; and subjecting the reaction product to desilylation reaction to give a quinazolinedione derivative having an ethoxycarbonylmethyl at the 1-position.

However, the above process ① to ③ are usually conducted at high temperature (150° C. or more) and by means of toxic reagents (e.g. phosgene, isocyanate, etc.), and they have many problems about yield and handling from an industrial point of view. Furthermore, the above process ④, which is represented by the following reaction scheme:

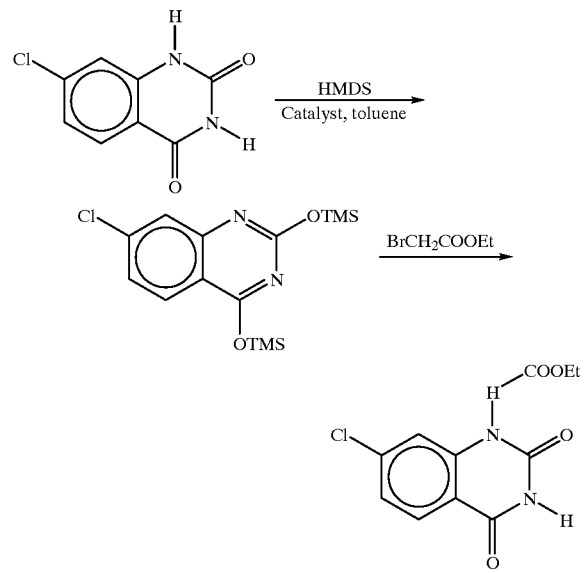

includes a lot of problems about the operation as follows:

(i) an irritant alkylating agent must be used to selectively subject the quinazolinedione derivative to alkylation reaction at the 1-position of the derivative in the first step;

(ii) because of alkylating of the 1-position of the derivative in the first step, it is required to subject the alkylated derivatives to the silylation reaction; and (iii) comparatively expensive anthranilic acid is used as a starting material.

Furthermore, an alkylating agent to be used in the above alkylation must be used in combination with a solvent to increase the yield of the desired intermediate.

Accordingly, it has been required to provide a process, which is superior in handling and safety, facilitates waste disposal, and makes it possible to obtain the desired intermediate at low cost. It has also been required to provide a process capable of efficiently obtaining 3-dihalobenzyl-2,4-quinazolinedione derivative as a final desired product by using this intermediate.

DISCLOSURE OF THE INVENTION

Accordingly, an object of the present invention is to provide a process capable of efficiently preparing a 3-dihalobenzyl-2,4-quinazolinedione derivative represented by the following formula (V) including a representative inhibitors against aldose reductases FK366.

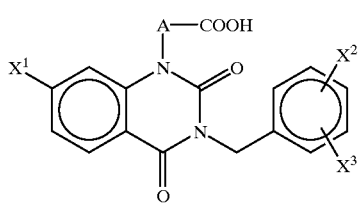

(V)

Another object of the present invention is to provide a novel process capable of preparing the compound (I), which is a useful intermediate for preparing the above compound (V), in a high yield and purity by using a simple operation under a moderate reaction condition.

BEST MODE FOR CARRYING OUT THE INVENTION

The present inventors have studied about a process of using 2,4-dihalobenzoic acid (VI) which is available easily to the industry, at low cost instead of comparatively expensive anthranilic acid conventionally used as the starting material to achieve the above object. However, a process of preparing the desired intermediate compound (I) in a high yield and purity through a compound (VIII) has never been known comprising selectively reacting the group at the 2-position of the above 2,4-dihalobenzoic acid (VI) with an amino acid derivative to give the compound (VIII).

The present inventors have intensively studied about the above process. As a result, by reacting 2,4-dihalobenzoic acid (VI) with an amino acid derivative in the presence of a copper containing catalyst, a derivative wherein a halogen at the 2-position of the above compound (VI) is selectively substituted could be obtained in a high yield and purity. Furthermore, the present inventors have found that the intermediate compound (I) useful for preparing FK366 (inhibitors against aldose reductases) can be obtained efficiently in a high yield under moderate condition by reacting the derivative obtained above with cyanic acid or its salts or urea and subjecting the reaction product to ring formation reaction. Thus, the present invention has been accomplished.

Furthermore, the present inventors have found a simple process capable of preparing 3-dihalobenzyl-2,4-quinazolinedione derivative (V) as the final desired product in a high yield and purity by means of the intermediate compound (I) thus obtained in one pot. That is, the present invention relates to a process characterized by conducting the following whole step in one pot comprising: introducing a carboxy protective group into the intermediate compound (I) as a starting material to give a compound having the carboxy protective group; reacting the compound obtained with a dihalobenzyl derivative in the presence of a suitable alcohol solvent to give a compound whose group at the 3-position is benzylated; and subjecting the compound obtained to elimination reaction of the carboxy protective group. Furthermore, the present inventors have intensively studied about the processes and found that a hydrogen atom of an imino group at the 3-position of the intermediate compound (I) can be selectively benzylated in the above process of the present invention. The whole preparation step of the final desired compound (V) of the present invention is illustrated as follows.

[a]

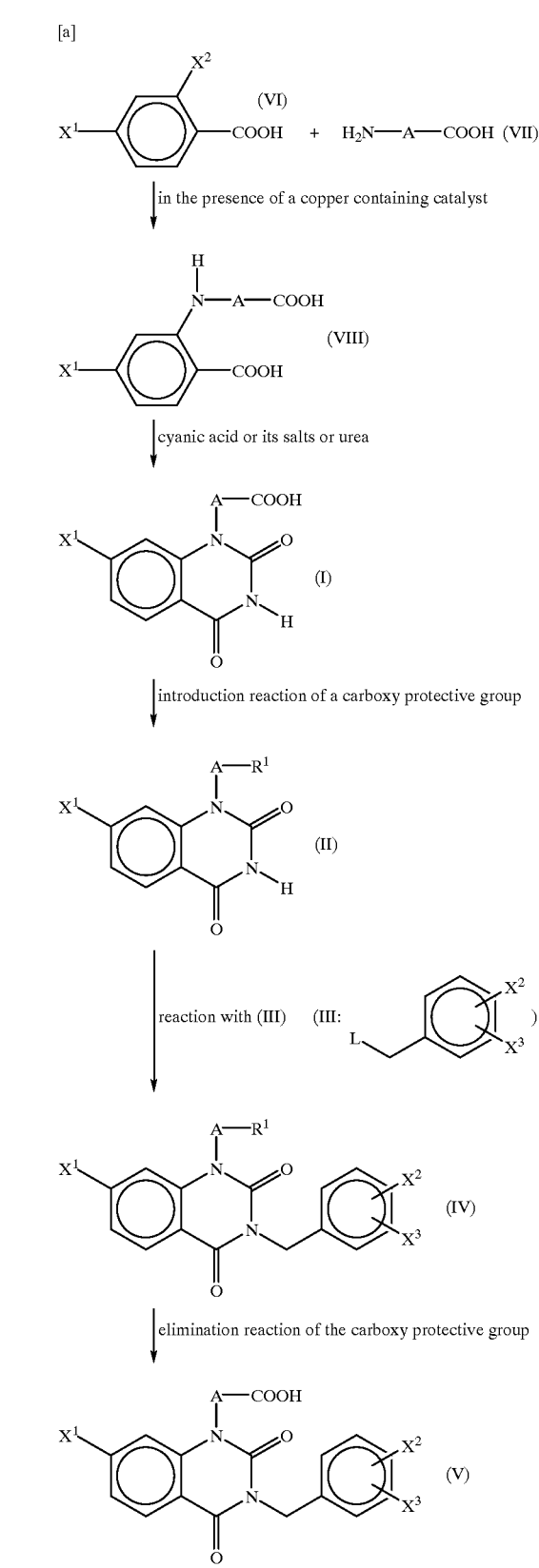

[b]

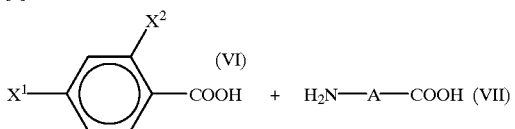

↓ in the presence of a copper containing catalyst

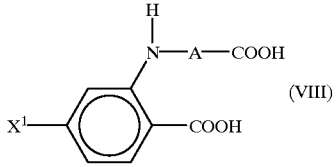

↓ cyanic acid or its salts or urea

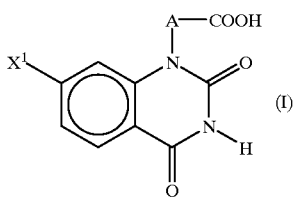

↓ reaction with (III)   (III: 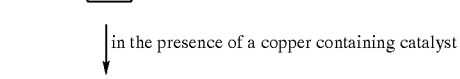 )

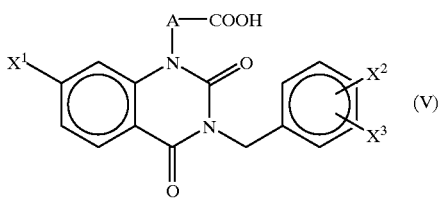

In obtaining the final desired compound (V), the process of preparing the compound of the formula (I) as an important intermediate can be roughly divided into two manners as follows.

[c]

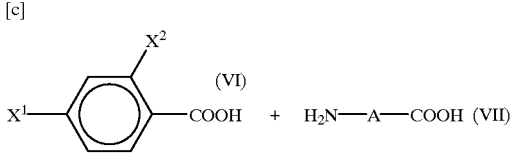

↓ in the presence of a copper containing catalyst

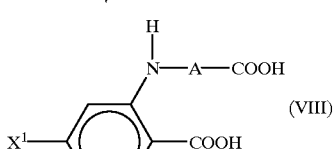

↓ cyanic acid or its salts or urea

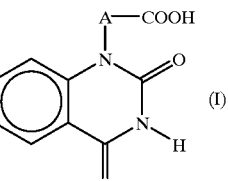

[d]

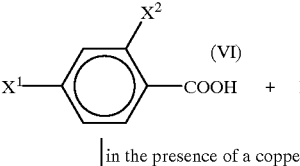

↓ in the presence of a copper containing catalyst

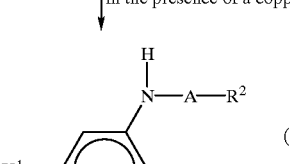

↓ cyanic acid or its salts or urea

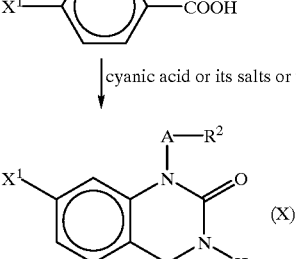

↓ hydrolysis reaction or oxidation reaction of $R^2$

(wherein
$X^1$, $X^2$ and $X^3$ are independently a halogen atom;
A is an alkylene group;
$R^1$ is a protected carboxy group;
$R^2$ is a group to be carboxy group by hydrolysis or oxidation;
L is an acid residue)

The above whole process is summarized as follows.
First, a process for preparing the final desired compound (V) can be divided into the following two manners:

Process A
① A step of introducing a carboxy protective group into the intermediate compound (I);
② without isolating the resulting reaction product, a step of reacting it with a dihalobenzyl derivative of the compound (III) to benzylate its 3-position group;
③ without isolating the resulting reaction product, a step of subjecting it to elimination reaction of the carboxy protective group to give the final desired compound (V).

Process B

①A step of directly reacting the intermediate compound (I) with a dihalobenzyl derivative compound (III) to give the final desired compound (V).

Furthermore, the intermediate compound (I) in the above process can be obtained by the following two processes roughly:

Process C

① A step of reacting an amino acid derivative of the compound (VII) with 2,4-dihalobenzoic acid of the compound (VI) in the presence of a copper containing catalyst to selectively substitute a halogen at the 2-position of the compound (VI) to give the compound (VIII), ② a step of comprising: reacting the resulting compound (VIII) with cyanic acid or its salts or urea and subjecting the reaction product to ring-closing reaction to give the intermediate compound (I).

Process D

①A step of comprising: reacting an amine derivative of the compound (XI) with 2,4-dihalobenzoic acid of the compound (VI) in the presence of a copper containing catalyst to selectively substitute a halogen at the 2-position of the compound (VI) to give the compound (IX), ② a step of reacting the resulting compound with cyanic acid or its salts or urea to give the compound (X), ③ a step of subjecting the resulting compound to hydrolysis reaction or oxidation reaction to give the intermediate compound (I).

In the first, each step for [Process A] is explained.

①A step of introducing a carboxy protective group into the intermediate compound (I) (Protection reaction of carboxy groups)

A carboxy protective group introduced into the intermediate compound (I) is not specifically limited, may be any one which can be easily introduced and easily removed after the reaction. For example, the above protection reaction includes protection by esterification. In detail, the intermediate compound (I) can be easily protected by subjecting it to esterification reaction within suitable temperature range in the presence of alcohols and acid.

As alcohols used in the above esterification, straight-chain or branched lower alcohols can be exemplified such as methanol, ethanol, propanol, butanol, isopropyl alcohol, or the like. Methanol and ethanol are particularly preferred because they can be easily treated after the reaction.

Preferred examples of the ester moiety of the esterificated carboxy group include lower alkyl ester such as methyl ester, ethyl ester, propyl ester, isobutyl ester, t-butyl ester, pentyl ester, hexyl ester, and the like. The lower alkyl ester may have at least one suitable substituent [e.g. lower alkanoyloxy (lower) alkyl ester, lower alkanesulfonyl (lower) alkyl ester, etc.].

The acid used in the above esterification is not specifically limited, may be any one which is usually used in the esterification reaction. Examples thereof include inorganic acid (e.g. hydrochloric acid, sulfuric acid and thionyl chloride, etc.), organic acid (e.g. tosyl acid, etc.), and the like.

The reaction time varies depending on the kind and amount of the reagent used in the reaction, reaction temperature, etc. is usually from several hours to 20 hours. After the completion of the reaction, a compound (II) can be isolated as a crystal by subjecting the acid catalyst to neutralization and treating further to remove, according to conventional methods.

This esterification reaction makes it possible to give the compound protected of carboxy group as a crystal in a exceedingly high yield and purity. If necessary, it can be isolated of the obtained product to give one in a higher purity.

② without isolating the resulting reaction product, a step of reacting it with a dihalobenzyl derivative of the compound (III) to benzylate its 3-position group (Benzylation at the 3-position)

A compound (IV) whose 3-position group is benzylated can be obtained in a high yield and purity by comprising: reacting the compound (II) obtained in the above ① with a dihalobenzyl derivative of the compound (III) in a lower alcohol solvent or, if necessary, in a mixed solvent with an inert solvent within suitable temperature range (preferably reflux temperature of the solvent) in the presence of a base (e.g., bicarbonate such as potassium bicarbonate, sodium bicarbonate, etc; carbonate such as potassium carbonate, sodium carbonate, etc.); and adjusting the pH of the reaction solution to the acidic side by conventional methods to give a crystal.

In the compound (III) used in this reaction, L is an acid residue. Examples thereof include halogen (fluorine, chlorine, bromine, iodine), sulfonate, etc. and halogen is preferable. It is preferred that the amount of the compound (III) is at least the same mol as that of the intermediate compound (I) as the starting material.

The solvent to be used is preferably the same alcohol as that used in the above ①. Methanol and ethanol are particularly preferable.

The reaction time varies depending on the kind and amount of the compound used in the reaction, the reaction temperature, etc. is usually from 30 minutes to 5 hours, and more preferably within several hours.

③ without isolating the resulting reaction product, a step of subjecting it to elimination reaction of the carboxy protective group to give the final desired compound (V) (Elimination reaction of carboxy protective group)

This reaction is conducted, for example, by hydrolysis in the presence of a base. Specifically, this reaction is conducted by adding a base or its solution in the reaction solution and hydrolyzing within the temperature range from room temperature to reflux temperature of the reaction solvent for 30 minutes to several hours.

Examples of the base used in the above reaction include hydroxides of alkali metals (e.g. potassium hydroxide, sodium hydroxide, etc.); bicarbonate of alkali metal (e.g. potassium bicarbonate, sodium bicarbonate, etc.); and carbonate of alkali metal (e.g. potassium carbonate, sodium carbonate, etc.), and the like. Among them, carbonate of alkali metal is preferable.

In preferable example of the compound (V) used in the above process, A is a methylene, $X^1$ is a chlorine atom, $X^2$ is a fluorine atom and $X^3$ is a bromine atom.

Since each step reaction in the above process makes it possible to give the products efficiently in a high purity, the whole process can be conducted in one pot without isolating the reaction intermediate obtained in each step.

The present inventors have further studied about modification of this process, as a result, found the process represented by the above process B. That is, the above process B comprises the process of reacting the intermediate compound (I) with a dihalobenzyl derivative of the compound (III) to selectively substitute a hydrogen atom of imino group at the 3-position of the quinazolinedione derivative with a benzyl group.

The kind of the solvent used in this reaction is not specifically limited, may be any one which is inert.

Examples thereof include water, methanol, ethanol, isopropyl alcohol, acetone, diethyl ether, THF, DMF, etc. and they can be used alone or in combination thereof. Examples of a preferable combination of the solvent include water-acetone, water-diethyl ether, water-methanol, and the like.

Examples of the base used in the present invention include hydroxide of alkali metal (e.g. lithium hydroxide, potassium hydroxide, sodium hydroxide, etc.), carbonate of alkali metal (e.g. potassium carbonate, sodium carbonate, etc.), bicarbonate of alkali metal (potassium bicarbonate, sodium bicarbonate, etc.), alkoxide of alkali metal (sodium ethoxide, potassium ethoxide, etc.), hydroxide of alkali earth metal (magnesium hydroxide, calcium hydroxide, etc.), or the like. These bases may be used alone or in combination thereof.

The amount of the compound (II) used in the above reaction is preferably at least the same mol as that of the intermediate compound (I). Considering the cost, the amount is preferably from 1 to 2 mols, and more preferably from 1 to 1.1 mols.

The reaction time varies depending on the kind and amount of the compound used, the kind of the base and solvent used, their amount, etc. is usually from 30 minutes to 5 hours, and more preferably from 30 minutes to 2 hours.

The reaction temperature also varies depending on the kind and amount of the compound used, the kind of the base and solvent used, their amount, the reaction time, etc. similar to the above reaction time. It is preferably from room temperature to 70° C.

Hereinafter, the process of preparing the intermediate compound (1) used in the present invention (the above processes C and D) is explained.

In the first, the process C is explained.

① A step of reacting an amino acid derivative of the compound (VII) with 2,4-dihalobenzoic acid of the compound (VI) in the presence of a copper containing catalyst to selectively substitute a halogen at the 2-position of the compound (VI) to give the compound (VIII)

For example, the compound (VIII) can be obtained in a high yield and purity by dissolving 1 to 3 eq. of compound (VII) and 1 eq. of the compound (VI) in a water medium, and reacting the solution at an suitable temperature within the range from 30° C. to reflux temperature of the solvent (more preferably 80° C. to reflux temperature) under strong base in the presence of a copper containing catalyst.

In the compound (VII), A is an alkylene, preferably an alkylene having from 1 to 12 carbon atoms, and more preferably an alkylene having from 1 to 6 carbon atoms.

Examples of the compound (VII) include fatty amino acid such as glycine, β-alanine, 4-aminobutanoic acid, 5-aminopentanoic acid, 6-aminohexanoic acid (or 6-aminocaproic acid), 7-aminoheptanoic acid, 8-aminooctanoic acid, 11-aminoundecanoic acid, 12-aminododecanoic acid, or the like.

Examples of the copper containing catalyst used in the present invention include copper or its salts. For example, copper powder; salts between copper and inorganic acid such as copper oxide, copper hydroxide, copper chloride, copper bromide, copper iodide, copper nitrate, copper sulfate, potassium copper chloride, etc.; salts between copper and organic acid such as copper acetate, copper cyanide, etc.; copper complex compound, etc. are exemplified. In the present invention, these copper containing catalysts can be used alone or in combination thereof.

The amount of the above copper containing catalyst varies depending on the kind of the compound and base used, the kind of the reaction solvent, the amount of them, the reaction temperature, the reaction time, or the like. It is preferably from 0.001 to 0.05% by weight, and more preferably from 0.004 to 0.05% by weight, based on the total weight of the compound (VI).

The reaction time also varies depending on the amount of the compound and catalyst used, reaction temperature, reaction solvent, or the like. It is usually from 30 minutes to 24 hours, and preferably from 30 minutes to several hours.

Furthermore, the pH of the reaction solution can be adjusted with an inorganic base or organic base. Examples of the inorganic base used in this reaction include hydroxide of alkali metal or alkali earth metal, bicarbonate of alkali metal or alkali earth metal, carbonate of alkali metal or alkali earth metal, and the like. Among them, examples of the hydroxide of alkali metal include lithium hydroxide, potassium hydroxide, sodium hydroxide, and the like; examples of the bicarbonate of alkali metal include lithium bicarbonate, potassium bicarbonate, sodium bicarbonate, and the like; and examples of the carbonate of alkali metal include lithium carbonate, potassium carbonate, sodium carbonate, and the like. An alkali metal salt of fatty acid such as sodium acetate, and the like can be also used. Further, examples of the hydroxide of alkali earth metal include calcium hydroxide, magnesium hydroxide, and the like; and examples of the carbonate of alkali earth metal include calcium carbonate, magnesium carbonate, and the like. In the present invention, they can be used alone or in combination thereof. Examples of the preferable combination include a combination of carbonate such as potassium carbonate, sodium carbonate, and the like and hydroxide such as potassium hydroxide, sodium hydroxide, and the like. A combination of potassium carbonate and potassium hydroxide is more preferable. Examples of the organic base used in the present invention include triethylamine, N-methylmorpholine, pyridine, lutidine, or the like. Of course in the present invention, the above inorganic base can be also used in combination with the organic base.

The order of adding the above compound (VI) and compound (VII) into the reaction solvent is not specifically limited.

② A step of comprising: reacting the resulting compound (VIII) with cyanic acid or its salts or urea and subjecting the reaction product to ring-closing reaction to give the intermediate compound (I)

1 eq. of the compound (VIII) obtained in the above ① is reacted with preferably from 1 to 10 eq., more preferably from 1 to 3 eq., and further more preferably 2 eq. of cyanic acid or its salts or urea. In the above, the reaction is preferably conducted at suitable temperature between room temperature to the boiling point of the reaction solvent under acidic side of pH 5 to 7 (more preferably pH 5.5 to 6.0, further more preferably pH 5.6 to 5.8) in the presence of water and, if necessary, an organic solvent such as diethyl ether, benzene, toluene, and the like. Then, the reaction solution is adjusted the pH to base (more preferably strong base) by means of the aforementioned base (e.g. sodium hydroxide, etc.), reacted at suitable temperature between room temperature to the boiling point of the reaction solvent (preferably from 30 to 40° C.) and treated the resulting reaction solution according to conventional methods to give the desired compound.

The time for reaction between the compound (VIII) and cyanic acid or its salts or urea varies depending on the kind of the compound (VIII) and cyanic acid or its salts or urea used, the kind and amount of the reaction solvent, pH of the reaction solution, the reaction temperature, or the like. It is usually from 30 minutes to 4 hours, and preferably from 30 minutes to 3.5 hours.

The reaction time for the ring closure (ring formation) varies depending on the basicity of the reaction solution, is usually from a few minutes to a few ten minutes. The ring formation is completed within 10 minutes under strong base condition.

Examples of the salts of the cyanic acid used in the present invention include alkali metal salts of the cyanic acid such as potassium cyanate, sodium cyanate, and the like; alkali earth metal salts such as barium cyanate, and the like; or silicon cyanate, lead cyanate, silver cyanate, mercury cyanate, uranyl potassium cyanate, and the like.

In the present invention, cyanic acid itself can be also used. Examples of the cyanic acid include those which is prepared by, for example, heating a cyanuric acid (prepared by rapid heating of urea) in the carbon dioxide stream, liquefying with freezing mixture to collect according to conventional methods.

Among them, use of the above salts of cyanic acid is recommended considering efficiency, safety, or the like.

Aforementioned process makes it possible to give the desired intermediate compound (I) in a high yield and purity and give its crystal easily, if the reaction solution is treated with acid. A higher purified product can be obtained, if necessary, by an additional recrystallization.

The above intermediate compound (I) can be also obtained according to the above Process D. This process is substantially the same as the above Process C, except that 2,4-dihalobenzoic acid of the compound (VI) is not reacted with an amino acid derivative of the compound (VII) in the above Process C, but reacted with the amine derivative of the formula (XI) and the reaction product is hydrolyzed or oxidized. That is, in the compound (IX), $R^2$ is a group to be a carboxy group by hydrolysis or oxidation. Examples thereof include hydroxymethyl group, cyano group, esters of the above aliphatic amino acid and their salts, or the like. The esters of the above fatty amino acid include preferably lower alkyl ester such as methyl, ethyl, propyl, isopropyl, butyl, and the like.

Examples of the compound of the formula (XI), wherein $R^2$ is a hydroxymethyl group, include ethanol amine, 3-amino-1-propanol, 4-amino-1-butanol, 5-amino-1-pentanol, 6-amino-1-hexanol, or the like. Examples of the compound of the formula (XI), wherein $R^2$ is a cyano group include, aminoacetonitrile, or the like.

In the case of using ethanol amine, aminoacetonitrile, etc. as the compound (IX), the desired intermediate compound (I) can be obtained by comprising: introducing an amino group into the 2-position of the compound (VI); subjecting the resultant compound to ring formation; and subjecting the resultant compound to oxidation reaction in the presence of nitric acid- nitrous acid, perchloric acid, etc. according to conventional methods.

Alternatively, the desired intermediate compound (I) can be obtained by comprising: introducing ethanol amine, etc. into the 2-position of the compound (VI); firstly subjecting the resultant compound to ring formation; secondly subjecting the resultant compound to oxidation reaction. In this case, the desired intermediate compound (I) can be also obtained from the reaction product with ethanol amine, aminoacetonitrile, etc. without isolating the reaction intermediate compound.

The following Examples further illustrate the present invention in detail but are not limited the scope thereof. The present invention may be practiced or embodied in still other ways without departing from the spirit or essential character thereof.

EXAMPLE 1

Process (I) for Preparing 2-carboxymethylamino-4-chlorobenzoic Acid (VIII)

To a solution of potassium carbonate (50.7 g), potassium hydroxide (47.3 g), 2,4-dichlorobenzoic acid (VI) (70 g) and glycine (VII) (96.3 g) in water (700 ml) was added cupric chloride (0.7 g) and the resulting solution was refluxed for 4 hours. After this reaction solution was cooled to 30° C., the copper salt was removed by filtration and concentrated hydrochloric acid (288 g) was added to the resultant filtrate at temperature of not more than 40° C. Then, the resulting precipitate was collected by filtration, washed with water and dried under vacuum to give 73.8 g of 2-carboxymethylamino-4-chlorobenzoic acid (yield, 87.7%).

mp.: 230.6° C.

H-NMR ($D_2O$—NaOD, δppm): 3.79(2H, s), 6.61–6.63 (1H, dd), 6.73(1H, d), 7.68–7.77(1H, d)

IR($cm^1$): 3368.12, 2895.50, 1705.28, 1624.26, 1568.32, 1505.62, 1427.50, 1297.29, 1234.59, 1143.93, 1112.10, 940.41, 920.16, 823.70, 797.66, 764.87, 674.20, 528.56

EXAMPLE 2

Process (2) for Preparing 2-carboxymethylamino-4-chlorobenzoic Acid (VIII)

This example was conducted using copper powder instead of cupric chloride in the above Example 1.

To a solution of potassium carbonate (10.3 g), potassium hydroxide (10.3 g), 2,4-dichlorobenzoic acid (VI) (15 g) and glycine (VII) (10.31 g) in water (150 ml) was added copper powder (0.38 g) and the resulting mixture was refluxed for 2 hours. Hereinafter, the resulting reaction solution was treated in the same manner as in Example 1 to give 12.8 g of the desired compound (yield, 71.2%).

EXAMPLES 3 to 18

The following Examples 3 to 18 were conducted by means of varying the amount of glycine, the kind and amount of the base, catalyst, and the like, the reaction temperature and time in the above Example 1 as shown in Table 1.

In the table, the amount of glycine (VII) and base represented by the molar ratio to 2,4-dichlorobenzoic acid (VI) of one mole, and the amount of the catalyst represented by the weight ratio (%) to compound (VI) used. The reaction yield is obtained as follows, that is, the desired compound (VIII) existing in the reaction solution was quantified by liquid chromatography.

TABLE 1

| Example No. | Amount of dichloro-benzoic acid (VI) (g) | Amount of glycine (molar ratio) | Amount of solvent (water) (ml) | Kind of base (amount) | | Kind of catalyst (amount) | Reaction temperature (° C.) | Reaction time (hr) | Reaction rate (%) |
|---|---|---|---|---|---|---|---|---|---|
| 3 | 5 | 3.50 | 10 | KOH (2.30) | $K_2CO_3$ (1.00) | $CuCl_2$ (0.01) | Reflux | 5 | 88.1 |
| 4 | 5 | 1.75 | 10 | KOH (1.90) | $K_2CO_3$ (0.80) | $CuCl_2$ (0.01) | Reflux | 4 | 83.8 |
| 5 | 5 | 1.75 | 11 | KOH (2.30) | $K_2CO_3$ (1.00) | $CuCl_2$ (0.01) | Reflux | 2 | 81.4 |
| 6 | 5 | 1.75 | 10 | KOH (2.30) | $K_2CO_3$ (1.00) | $CuCl_2$ (0.01) | Reflux | 4 | 79.4 |
| 7 | 5 | 1.75 | 10 | KOH (2.30) | $K_2CO_3$ (1.00) | $CuCl_2 \cdot 5H_2O$ (0.02) | Reflux | 5 | 82.3 |
| 8 | 5 | 1.75 | 10 | KOH (2.30) | $K_2CO_3$ (1.00) | $Cu(AcO)_2 \cdot 1H_2O$ (0.02) | Reflux | 5 | 81.2 |
| 9 | 5 | 1.75 | 10 | KOH (2.30) | $K_2CO_3$ (1.00) | $CuCl_2$ (0.01) | Reflux | 3 | 82.2 |
| 10 | 5 | 1.75 | 10 | KOH (2.30) | $K_2CO_3$ (0.95) | Cu (0.025) | 80–85 | 6 | 80.0 |
| 11 | 5 | 1.75 | 10 | — | $K_2CO_3$ (2.00) | $CuCl_2$ (0.01) $LiCl_2$ (0.03) | Reflux | 6 | 82.9 |
| 12 | 5 | 1.75 | 10 | KOH (1.84) | $K_2CO_3$ (0.80) | Cu (0.01) | Reflux | 5 | 84.6 |
| 13 | 5 | 2.50 | 10 | KOH (1.90) | $K_2CO_3$ (0.80) | $CuCl_2$ (0.004) | Reflux | 5 | 85.6 |
| 14 | 15 | 1.75 | 10 | AcONa (1.90) | KOH (2.34) | Cu (0.025) | Reflux | 3 | 63.5 |
| 15 | 5 | 1.75 | 10 | $KHCO_3$ (3.5) | — | $CuCl_2$ (0.01) | Reflux | 5 | 79.8 |
| 16 | 5 | 3.5 | 10 | $Et_3N$ (3) | $KHCO_3$ (1.2) | $CuCl_2$ (0.01) | Reflux | 21 | 82.9 |
| 17 | 10 | 3.5 | 6 | $Na_2CO_3$ (2.2) | — | $CuCl_2$ (0.01) | Reflux | 5 | 95.1 |
| 18 | 5 | 3.5 | 6 | N-methyl-morpholine (4) | | $CuCl_2$ (0.01) | Reflux | 6 | 60.7 |

EXAMPLE 19

Process for Preparing 2-carboxypentylamino-4-chlorobenzoic Acid (VIII)

To a solution of potassium carbonate (3.62 g), potassium hydroxide (3.38 g), 2,4-dichlorobenzoic acid (VI) (5.0 g) and 6-amino-n-caproic acid (13.8 g) in water (50 ml) was added cupric chloride (0.05 g) and the resulting solution was refluxed for 18 hours. After this reaction solution was cooled to room temperature, the copper salt was removed by filtration and concentrated hydrochloric acid (25 ml) was added to the resulting filtrate. Then; the resulting precipitate was collected by filtration, washed with water and dried under vacuum to give 4.8 g of the desired compound (yield, 64%).

mp.: 206.5° C. (20% water-containing methanol)

H-NMR (DMSO-$d_6$, δ ppm): 1.27–1.72(6H, m), 2.16–2.31(2H, t), 3.1–3.3(2H, m), 6.5–6.62(1H, d, d), 6.72–6.74(1H, d), 7.73–7.83(1H, d)

IR(cm$^{-1}$): 3356.55, 2949.52, 2861.75, 2363.09, 1686.95, 1639.69, 1572.18, 1507.55, 1477.65, 1461.26, 1411.10, 1388.92, 1308.86, 1294.39, 1236.62, 1161.29, 1117.88, 1104.38, 924.98, 843.00, 778.37, 741.72, 698.32, 667.45, 583.54, 522.77, 451.40

EXAMPLE 20

Process (I) for Preparing 7-chloro-1-carboxymethyl-2,4 (1H, 3H)-quinazolinedione (I)

A solution of 2-carboxymethylamino-4-chlorobenzoic acid (VIII) (5 g), 25% aqueous sodium hydroxide (8.57 g) and sodium cyanate (1.67 g) in water (65 ml) was reacted at 35° C. for one hour, adjusting to pH 5.7 with concentrated hydrochloric acid. Then, the reaction was conducted by 5 times-addition of sodium cyanate (0.42 g) every 30 minutes. 25% aqueous sodium hydroxide (7.88 g) was added to this reaction solution, the reaction was conducted at 60 to 65° C. for one hour, and then concentrated hydrochloric acid (12.8 g) was added at 60° C., the resulting crystal was collected by filtration, washed with water and dried under vacuum to give 4.78 g of 7-chloro-1-carboxymethyl-2,4 (1H, 3H)-quinazolinedione (yield, 87.6%).

mp.: 305.5° C.

H-NMR ($D_2O$-NaOD, δ ppm): 4.57(2H, s), 7.01–7.08 (1H, dd), 7.18(1H, d), 7.78–7.88(1H, d)

IR(cm$^{-1}$): 3048.86, 1737.11, 1694.67, 1607.86, 1468.01, 1396.63, 1309.83, 1278.00, 1201.80, 1084.13, 937.52, 835.28, 776.44, 441.75

EXAMPLE 21

Process (2) for Preparing 7-chloro-1-carboxymethyl-2,4(1H, 3H)-quinazolinedione

To a suspension of 2-carboxymethylamino-4-benzoic acid (VIII) (7 g) in water (60 ml) was added 25% aqueous sodium hydroxide (5.95 g) to adjust to pH 5.7. A solution of sodium cyanate (4.58 g) in water (37 ml) was added dropwise to the resulting solution at 35° C. over 2.5 hours. During this dropwise addition, the pH of the reaction solution was adjusted to 5.7 with concentrated hydrochloric acid. After the completion of dropping, the reaction was further continued at the same temperature and pH for one hour. Then, 25% aqueous sodium hydroxide (10.8 g) was added in the solution and the resulting solution was reacted at 60° C. for 10 minutes, hereinafter, was treated in the same manner as in Example 20 to give 6.0 g of the desired compound (yield, 80.3%).

EXAMPLE 22

Process (3) for Preparing 7-chloro-1-carboxymethyl-2,4 (1H, 3H)-quinazolinedione (I)

To a suspension of 2-carboxymethylamino-4-chlorobenzoic acid (VIII) (3.5 g) in water (68 ml) was added 25% aqueous sodium hydroxide (2.47 g)to adjust to pH 5.0. Sodium cyanate (4.77 g) was added to the resulting solution and the resulting solution was reacted at 35° C. for one hour, adjusting the pH to 6.0 with concentrated hydrochloric acid. Then, to the reaction solution was added 25% aqueous sodium hydroxide (5.4 g) and the resulting solution was reacted at 60° C. for 10 minutes. The resulting reaction solution was treated in the same manner as in Example 21 to give 2.65 g of the desired compound (yield, 70.9%).

EXAMPLE 23

Process for Preparing 2-(2-hydroxyethylamino)-4-chlorobenzoic Acid (IX)

This example was conducted to give the above desired product by using ethanolamine instead of glycine used in the above Example 1.

First, 2,4-dichlorobenzoic acid (VI) (19.1 g) and cupric chloride (200 mg) were added to ethanolamine (XI) (36.6 g) and the solution was reacted at 80 to 90° C. for 4.5 hours. After the reaction, the pH of the reaction solution was adjusted to 1 by addition of concentrated hydrochloric acid, and then the resulting precipitate was collected by filtration to give 20.9 g of 2-(2-hydroxyethylamino)-4-chlorobenzoic acid (IX) (yield, 97%).

H-NMR ($\delta$ ppm, $CDCl_3$: $CD_3OD$=1:1): 3.34(2H, t), 3.80 (2H, t), 6.55(d-d, 1H), 6.73(1H, d), 7.87(1H, d)

EXAMPLE 24

Process for Preparing 1-(2-hydroxyethyl)-7-chloro-2,4 (1H, 3H)-quinazolinedione (X)

To a suspension of 2-(2-hydroxyethylamino)-4-chlorobenzoic acid (5.0 g) in water (50 ml) was added lithium hydroxide (1.0 g), was further added sodium cyanate (1.05 g) with maintaining the temperature at about 40° C. The resulting solution was reacted for 2 hours, adjusting the pH 6.0–7.0 with concentrated hydrochloric acid. Then, to the reaction solution was added lithium hydroxide (1.3 g), was further added sodium cyanate (2.1 g) at the same temperature, the resulting solution was reacted for one hour. Then, the reaction mixture was reacted for further 4 hours with adjusting the pH in the same manner as above. After the reaction, to the reaction solution was added lithium hydroxide (1.7 g) and was reacted for further 3 hours. Concentrated hydrochloric acid (5 ml) was added to this reaction solution, the resulting crystal was collected by filtration to give 4.69 g of 1-(2-hydroxyethyl)-7-chloro-2,4(1H, 3H)-quinazolinedione (yield, 84.1%).

H-NMR ($\delta$ ppm, $CD_3OD$:$CDCl_3$=5:1): 3.87(2H, t), 4.27 (2H, t), 5.24(2H, s), 7.2–7.5(6H, m), 7.60(1H, d), 8.12(1H, d).

EXAMPLE 25

Process for Preparing 1-carboxymethyl-7-chloro-2,4 (1H, 3H)-quinazolinedione (I)

1-(2-hydroxyethyl)-7-chloro-2,4 (1H, 3H)-quinazolinedione obtained in the above Example 24 was added in 60% nitric acid (8 ml), sodium nitrite (250 mg) was further added at 65° C. and the reaction solution was reacted for one hour. Then, sodium nitrite (250 mg) was further added and the reaction solution was reacted for 3 hours. After the reaction, ice water (10 ml) was added and the resulting crystal was collected by filtration to give 700 mg of 1-carboxymethyl-7-chloro-2,4(1H, 3H)-quinazolinedione (yield, 67%).

EXAMPLE 26

Process for Preparing 1-carboxymethyl-7-chloro-2,4 (1H, 3H)-quinazolinedione (I)

In this Example, the ring formation reaction was conducted by using urea instead of cyanate.

First, to a suspension of 2-carboxymethylamino-4-chlorobenzoic acid (VIII) (0.5 g) in water (10 ml) was added 25% aqueous sodium hydroxide (0.85 g) to adjust to pH 6.8 with concentrated hydrochloric acid. Then, urea (2.54 g) was added, the resulting solution was reacted at reflux temperature for 21 hours (pH 10 at that time), concentrated hydrochloric acid was added to give a crystal. The resulting crystal was collected by filtration, washed with water and dried to give 324 mg of 1-carboxymethyl-7-chloro-2,4(1H, 3H)-quinazolinedione (yield, 60%).

EXAMPLE 27

Process (I) for Preparing 7-chloro-1-ethoxycarbonylmethyl-2,4 (1H, 3H)-quinazolinedione (II)

To a suspension of 1-carboxymethyl-7-chloro-2,4(1H, 3H)-quinazolinedione (I) (0.5 g) in ethanol (10 ml) was added thionyl chloride (0.35 g) at 0° C. After one drop of concentrated sulfuric acid was added to the solution, the solution was refluxed for 7 hours, and cooled. The resulting crystal was collected by filtration, washed with ethanol and dried under vacuum to give 0.42 g of the desired compound (yield, 75.8%).

mp.: 255.8° C.

H-NMR (DMSO-$D_6$, $\delta$ ppm): 1.15–1.31 (3H, t), 4.07–4.30(2H, q), 4.92(2H, s), 7.28–7.39(1H, dd), 7.58–7.60 (1H, d), 7.97–8.07(1H, d)

IR($cm^{-1}$): 3185.83, 3058.51, 1744.83, 1713.96, 1694.67, 1604.97, 1581.82, 1455.47, 1432.32, 1415.92, 1389.88, 1302.11, 1234.59, 1215.30, 1144.89, 1081.23, 1024.33, 934.62, 884.47, 854.57, 776.44, 751.37, 716.64, 673.24, 567.14, 545.92, 486.76, 439.82

EXAMPLE 28

Process (2) for Preparing 7-chloro-1-ethoxycarbonylmethyl-2,4(1H, 3H)-quinazolinedione (II)

To a suspension of 1-carboxymethyl-7-chloro-2,4(1H, 3H)-quinazolinedione (I) (5 g) in ethanol (50 ml) was added concentrated sulfuric acid (0.96 g) at room temperature, and the reaction solution was refluxed for 19 hours. After the reaction solution was concentrated suitablely to half, water (25 ml) was added, 10% potassium bicarbonate solution (25 g) was further added to adjust to pH 8. The resulting crystal was collected by filtration, washed with water and dried under vacuum to give 4.55 g of the desired compound (yield, 82%).

EXAMPLE 29

Process for Preparing 7-chloro-1-methoxycarbonylmethyl-2,4(1H, 3H)-quinazolinedione (II)

To a suspension of 1-carboxymethyl-7-chloro-2,4(1H, 3H)-quinazolinedione (1) (5 g) in methanol (70 ml) was added concentrated sulfuric acid (1.92 g) at room temperature, and the reaction solution was refluxed for 20 hours. After the reaction solution was concentrated suitablely to half, water (20 ml) was added to adjust to pH 9 with 20% potassium carbonate solution (27 g). The resulting crystal was collected by filtration, washed with water and dried under vacuum to give 4.56 g of the desired compound (yield, 86.5%).

mp.: 276.2° C.

IR(cm$^{-1}$): 3169.43, 3041.15, 2961.09, 2835.70, 1745.79, 1715.89, 1693.71, 1608.83, 1583.75, 1505.62, 1462.22, 1443.89, 1433.28, 1422.67, 1393.74, 1374.45, 1305.97, 1243.27, 1220.12, 1151.64, 1107.27, 1084.13, 980.92, 936.55, 861.32, 831.42, 774.51, 753.29, 693.49, 673.24

EXAMPLE 30

Process (I) for Preparing 3-[(4-bromo-2-fluoro)benzyl]-1-carboxymethyl-7-chloro-2,4(1H, 3H)-quinazolinedione (V)

To a solution of 7-chloro-1-ethoxycarbonylmethyl-2,4 (1H, 3H)-quinazolinedione (II) (1.41 g) in ethanol (20 ml) were added potassium carbonate (0.83 g) and 4-bromo-2-fluoro-benzylbromide (III) (1.74 g) with stirring, and the solution was refluxed for 3 hours. Then, aqueous sodium hydroxide (0.2 g/20 ml) was added to the reaction solution, the resultant was refluxed for 1.5 hours. Aqueous hydrochloric acid [concentrated hydrochloric acid (5 ml) in water (30ml)] was added to the reaction solution to adjust to pH 1. The resulting precipitate was collected by filtration, washed with water, washed with 50% isopropyl alcohol and filtrated to give 1.99 g of the desired compound (yield, 90.1%).

mp.: 224.6° C.

H-NMR (DMSO-d$_6$, δ ppm): 4.91(2H, s), 5.14(2H, s), 7.05–7.66(5H, m), 8.08(1H, d, J=8.55Hz)

IR(cm$^{-1}$): 3087.45, 1716.85, 1664.77, 1605.93, 1581.82, 1489.23, 1464.15, 1427.50, 1386.99, 1359.02, 1310.79, 1291.50, 1266.42, 1241.34, 1221.09, 1162.25, 1112.10, 1096.67, 979.00, 916.30, 873.86, 841.07, 816.95, 789.95, 770.66, 762.94, 737.86, 669.38, 576.79, 472.62

EXAMPLE 31

Process (2) for Preparing 3-[(4-bromo-2-fluoro)benzyl]-1-carboxymethyl-7-chloro-2,4(1H, 3H)-quinazolinedione (V)

A mixture of 1-carboxymethyl-7-chloro-2,4(1H, 3H)-quinazolinedione (II) (1.27 g) and concentrated sulfuric acid (0.49 g) in methanol (28 ml) was reacted at reflex temperature for 19 hours. Then, potassium carbonate (1.38 g) and 4-bromo-2-fluorobenzylbromide (III) (1.74 g) were added with stirring, the reaction solution was reacted at reflux temperature for 3 hours. Aqueous sodium hydroxide (0.2 g/20 ml) was added to the reaction solution, the resultant was refluxed for one hour. After the reaction, concentrated hydrochloric acid (5 ml) was added to the reaction solution to adjust to pH 1. The resulting precipitate was collected by filtration, washed with water, washed with 50% methanol and filtrated to give 1.56 g of the desired compound (yield, 70.7%)

EXAMPLE 32

Process (3) for preparing 3-[(4-bromo-2-fluoro)benzyl]-1-carboxymethyl-7-chloro-2,4(1H, 3H)-quinazolinedione (V)

To a solution of 1-carboxymethyl-7-chloro-2,4(1H, 3H)-quinazolinedione (640 mg) and sodium hydroxide (248 mg) in water (5 ml) was added dropwise a solution of 4-bromo-2-fluorobenzylbromide (473 mg) in acetone with stirring at 40° C., and the reaction solution was reacted for 6 hours. After the reaction, the pH of the reaction solution was acidified and the resulting crystal was collected by filtration to give 0.99 g of 3-[(4-bromo-2-fluoro)benzyl]-1-carboxymethyl-7-chloro-2,4(1H, 3H)-quinazolinedione (yield, 89%).

Industrial Applicability

The process of the present invention enables the efficient preparation of a 3-dihalobenzyl- 2,4-quinazolinedione derivative of the formula (V) useful as inhibitors against aldose reductases, makes it possible to secure the safety and hygiene of workers, and to reduce the cost because of unnecessity of waste disposal, therefore, being industrially exceedingly advantageous.

Specifically, in preparing of the intermediate compound (I), the process of the present invention has the following advantages.

①  In the present invention, 2,4-dichlorobenzoic acid could be used as the starting material to selectively introduce an amino group into the 2-position of the benzoic acid in a high yield. 2,4-dichlorobenzoic acid is industrially available and a cheap starting material, therefore, it has made possible to prepare the desired intermediate compound easily at exceedingly low cost.

②  The process of the present invention is superior in handling and safety because of using no irritant halide (e.g. halogeno acetate, etc.), or the like. Furthermore, it is extremely simple and efficient because of not using expensive silylating agents used conventionally.

③  The waste disposal is easy because of using mainly water as the reaction solvent.

④  The intermediate compound (I) obtained according to the process of the present invention can be reacted with suitable alcohols to give an optional ester derivative.

Furthermore, in the process of the final desired compound (V) using the above intermediate compound (I), the reaction product of each step can be obtained in a high yield and purity, without isolating the reaction product, in one pot. Moreover, it has made possible to selectively benzylate a hydrogen atom of the imino group at the 3-position of the quinazolinedione ring. This process is superior in handling and exceedingly useful from the viewpoint of efficiency, and the safety and hygiene of workers.

What is claimed is:

1. A process for preparing a 3-dihalobenzyl-2,4-quinazolinedione compound represented by the formula (V):

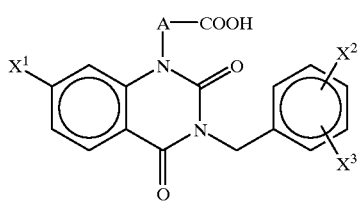

(V)

which comprises:

reacting a dihalobenzyl compound represented by the formula (III):

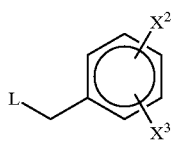

(III)

with a 2,4-quinazolinedione compound having a carboxyalkyl group represented by the formula (I):

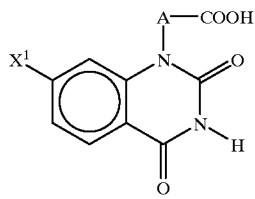

(I)

in the presence of a water-containing solvent, to selectively substitute a hydrogen atom of an imino group at the 3-position of the compound (I), wherein, in the above formulae, $X^1$, $X^2$, and $X^3$ are independently halogen, A is methylene, and L is a halogen.

2. A process for preparing a 3-dihalobenzyl-2,4-quinazolinedione compound represented by the formula (V):

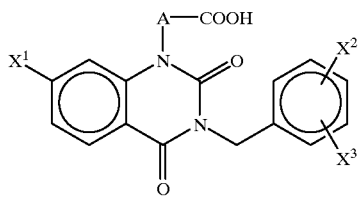

(V)

which comprises:

reacting a 2-carboxyalkylamino-4-halobenzoic acid compound represented by the formula (VIII):

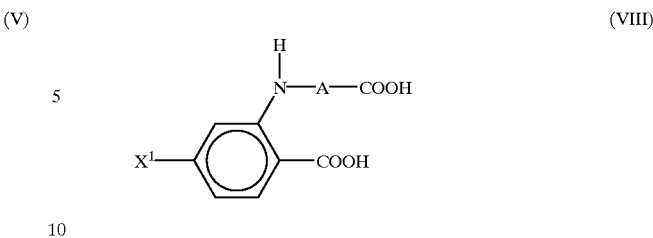

(VIII)

with cyanic acid or its salts or urea to give a 2,4-quinazolinedione compound having a carboxyalkyl group represented by the formula (I):

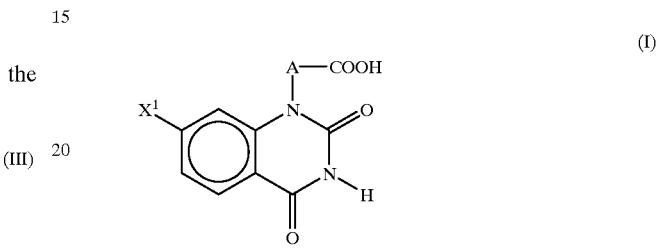

(I)

introducing a carboxy protective group into the 2,4-quinazolinedione compound (I);

without isolating the resulting reaction products, reacting it with a dihalobenzyl compound represented by the formula (III):

(III)

and without isolating the resulting reaction product, subjecting it to elimination reaction of the carboxy protective group, wherein, in the above formulae, $X^1$, $X^2$, and $X^3$ are independently halogen, A is methylene, and L is a halogen.

3. A process for preparing a 3-dihalobenzyl-2,4-quinazolinedione compound represented by the formula (V):

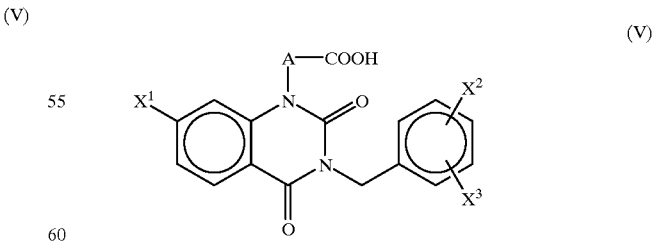

(V)

which comprises:

reacting a 2-carboxyalkylamino-4-halobenzoic acid compound represented by the formula (VIII):

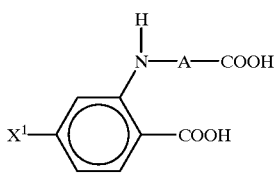

(VIII)

with cyanic acid or its salts or urea to give a 2,4-quinazolinedione compound having a carboxyalkyl group represented by the formula (I):

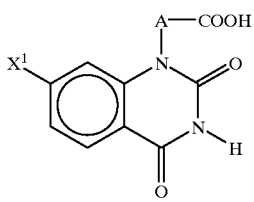

(I)

and reacting the 2,4-quinazolinedione compound (I) with a dihalobenzyl compound represented by the formula (III):

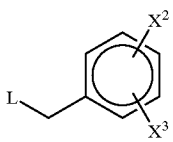

(III)

to selectively substitute a hydrogen atom of an imino group at the 3-position of the compound (I), wherein, in the above formulae, $X^1$, $X^2$, and $X^3$ are independently halogen, A is methylene, and L is a halogen.

4. A process for preparing a 3-dihalobenzyl-2,4-quinazolinedione compound represented by the formula (V):

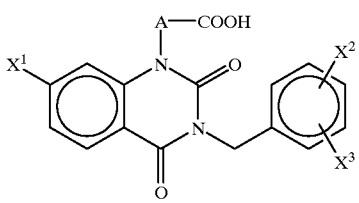

(V)

which comprises:

reacting an amino acid compound represented by the formula (VII):

$H_2N-A-COOH$ (VII)

with a 2,4-dihalobenzoic acid compound represented by the formula (VI):

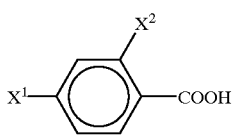

(VI)

in the presence of a copper containing catalyst to selectively substitute a halogen at the 2-position of the compound (VI) to give a 2-carboxyalkylamino-4-halobenzoic acid compound represented by the formula (VIII):

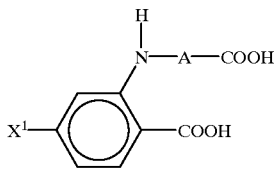

(VIII)

and reacting the 2-carboxyalkylamino-4-halobenzoic acid compound (VIII) with cyanic acid or its salts or urea to give a 2,4-quinazolinedione compound having a carboxyalkyl group represented by the formula (I):

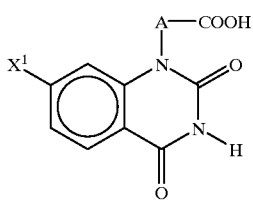

(I)

without isolating the resulting reaction product, introducing a carboxy protective group into the compound (I); and reacting the resulting reaction product with a dihalobenzyl compound represented by the formula (III):

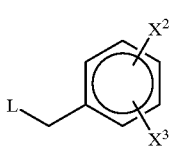

(III)

and without isolating the resulting reaction product, subjecting the product to elimination reaction of the carboxy protective group, wherein, in the above formulae, $X^1$, $X^2$, and $X^3$ are independently halogen, A is methylene, and L is a halogen.

5. A process for preparing a 3-dihalobenzyl-2,4-quinazolinedione compound represented by the formula (V):

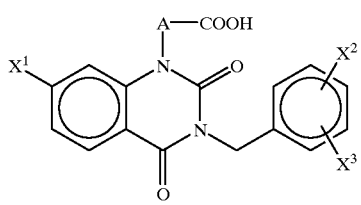
(V)

which comprises:

reacting an amino acid compound represented by the formula (VII):

H$_2$N—A—COOH  (VII)

with a 2,4-dihalobenzoic acid compound represented by the formula (VI):

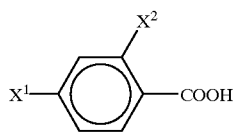
(VI)

in the presence of a copper containing catalyst to selectively substitute a halogen at the 2-position of the compound (VI) to give a 2-carboxyalkylamino-4-halobenzoic acid compound represented by the formula (VIII):

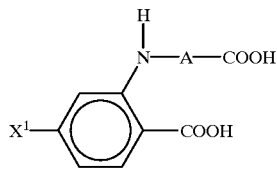
(VIII)

reacting the 2-carboxyalkylamino-4-halobenzoic acid compound with cyanic acid or its salts or urea to give a 2,4-quinazolinedione compound having a carboxyalkyl group represented by the formula (I):

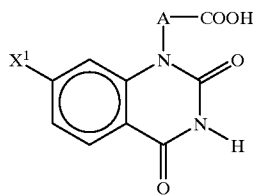
(I)

and reacting the compound (I) with a dihalobenzyl compound represented by the formula (III):

(III)

to selectively substitute a hydrogen atom of imino group at the 3-position of the compound (I), wherein, in the above formulae, $X^1$, $X^2$, and $X^3$ are independently halogen, A is methylene, and L is a halogen.

6. A process for preparing a quinazolinedione compound having a carboxyalkyl group represented by the formula (I):

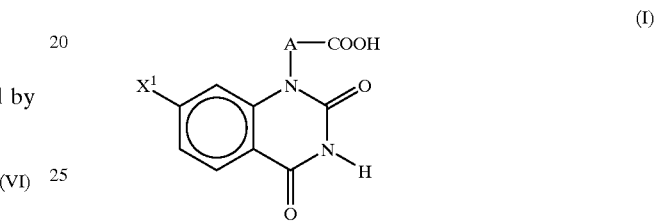
(I)

which comprises reacting a 2-carboxyalkylamino-4-halobenzoic acid compound represented by the formula (VIII):

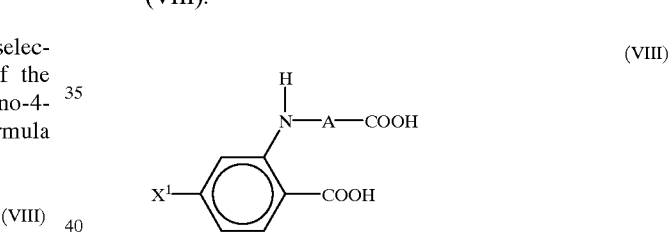
(VIII)

with cyanic acid or its salts or urea, wherein, in the above formulae, $X^1$ is halogen and A is methylene.

7. A process for preparing a quinazolinedione compound having a carboxyalkyl group represented by the formula (I):

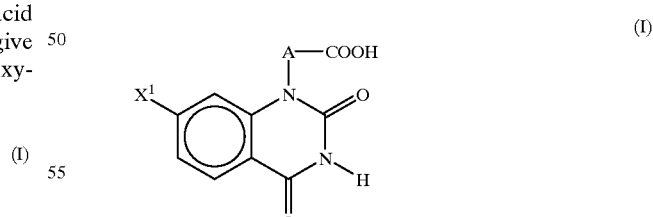
(I)

which comprises:

reacting an amino acid compound represented by the formula (VII):

H$_2$N—A—COOH  (VII)

with a 2,4-dihalobenzoic acid compound represented by the formula (VI):

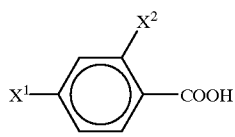

(VI)

in the presence of a copper containing catalyst to selectively substitute a halogen at the 2-position of the compound (VI) to give a 2-carboxyalkylamino-4-halobenzoic acid compound represented by the formula (VIII):

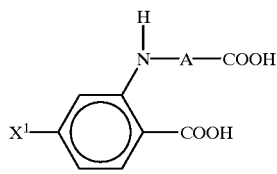

(VIII)

and reacting the 2-carboxyalkylamino-4-halobenzoic acid compound with cyanic acid or its salts or urea, wherein, in the above formulae, $X^1$ and $X^2$ are independently halogen, and A is methylene.

8. A process for preparing a 2-carboxyalkylamino-4-halobenzoic acid compound represented by the formula (VIII):

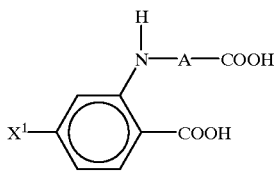

(VIII)

which comprises reacting an amino acid compound represented by the formula (VII):

$H_2N-A-COOH$ (VII)

with a 2,4-dihalobenzoic acid compound represented by the formula (VI):

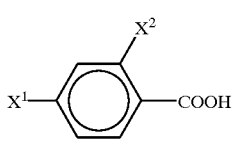

(VI)

in the presence of a copper containing catalyst to selectively substitute a halogen at the 2-position of the compound (VI), wherein, in the above formulae, $X^1$ and $X^2$ are independently halogen, and A is methylene.

9. The process of claim 1, wherein said water-containing solvent is water-acetone.

* * * * *